(12) United States Patent
Asano et al.

(10) Patent No.: US 10,543,143 B2
(45) Date of Patent: Jan. 28, 2020

(54) GAIT DATA MANAGEMENT SYSTEM, GAIT DATA MANAGEMENT METHOD, WALKING ASSISTANCE DEVICE AND SERVER

(71) Applicant: Panasonic Corporation, Osaka (JP)

(72) Inventors: Katsuhisa Asano, Nara (JP); Motoki Nakano, Kyoto (JP); Hiromichi Fujimoto, Nara (JP)

(73) Assignee: PANASONIC CORPORATION, Osaka (JP)

( * ) Notice: Subject to any disclaimer, the term of this patent is extended or adjusted under 35 U.S.C. 154(b) by 294 days.

(21) Appl. No.: 15/509,743

(22) PCT Filed: Aug. 26, 2015

(86) PCT No.: PCT/JP2015/004295
§ 371 (c)(1),
(2) Date: Mar. 8, 2017

(87) PCT Pub. No.: WO2016/038824
PCT Pub. Date: Mar. 17, 2016

(65) Prior Publication Data
US 2017/0252255 A1    Sep. 7, 2017

(30) Foreign Application Priority Data

Sep. 10, 2014  (JP) .................................. 2014-184654

(51) Int. Cl.
*A61H 3/00* (2006.01)
*A61F 2/68* (2006.01)
*A61F 2/70* (2006.01)

(52) U.S. Cl.
CPC .................. *A61H 3/00* (2013.01); *A61F 2/68* (2013.01); *A61F 2002/701* (2013.01);
(Continued)

(58) Field of Classification Search
CPC ....................................................... A61H 3/00
See application file for complete search history.

(56) References Cited

U.S. PATENT DOCUMENTS

2006/0184280 A1    8/2006    Oddsson et al.

FOREIGN PATENT DOCUMENTS

| JP | 2010-263934 | 11/2010 |
| JP | 2012-90651 | 5/2012 |

OTHER PUBLICATIONS

Extended European Search Report dated Apr. 26, 2018 in European Patent Application No. 15840039.0.
(Continued)

*Primary Examiner* — Matthew W Schall
(74) *Attorney, Agent, or Firm* — Wenderoth, Lind & Ponack, L.L.P.

(57) ABSTRACT

A server of a gait data management system includes: an obtaining unit that obtains a first sensor value obtained when a walker walks with assistance from a walking assistance device; an accumulating unit that accumulates the first sensor value, and the walking assistance device includes: an actuator that drives a joint; a storage unit that stores a walk algorithm that is for determining a drive level of the actuator and is generated through statistical processing on a gait value indicating walking characteristics and calculated from the first sensor value accumulated in the accumulating unit; a sensor that obtains a second sensor value obtained when the walker walks with assistance from the walking assistance device; a control unit that determines the drive level of the actuator according to the second sensor value using the walk algorithm; and a transmitting unit that transmits the second sensor value to the server.

9 Claims, 9 Drawing Sheets

(52) U.S. Cl.
CPC .. *A61F 2002/704* (2013.01); *A61H 2201/501* (2013.01); *A61H 2201/5058* (2013.01)

(56) References Cited

OTHER PUBLICATIONS

International Search Report dated Oct. 13, 2015 in International Application No. PCT/JP2015/004295.

FIG. 10

| Type | Level walking | Uphill walking | Downhill walking |
|---|---|---|---|
| Stride (left) | 50 cm | 45 cm | 43 cm |
| Stride (right) | 51 cm | 46 cm | 43 cm |
| Period | 0.5 sec | 0.5 sec | 0.4 sec |

FIG. 11

| Body type | Short height | Medium height | High height |
|---|---|---|---|
| Stride (left) | 45 cm | 50 cm | 55 cm |
| Stride (right) | 46 cm | 51 cm | 56 cm |
| Period | 0.4 sec | 0.5 sec | 0.6 sec |

GAIT DATA MANAGEMENT SYSTEM, GAIT DATA MANAGEMENT METHOD, WALKING ASSISTANCE DEVICE AND SERVER

TECHNICAL FIELD

The present invention relates to a gait data management system, a gait data management method, a walking assistance device, and a server.

BACKGROUND ART

There are walking assistance devices that are fitted onto persons and provide walking assistance for the persons fitted with the walking assistance devices (hereinafter, referred to as walkers). The walking assistance devices are mainly fitted onto walkers' legs (lower body). The walking assistance devices include structures formed from a rigid member and joints, and drive the joints with motive power generated by a source of motive power, to assist a walker in making a walking movement.

The walking assistance devices obtain a movement of a walker's leg by using a sensor and adjust the level, timing, etc., of motive power which the source of motive power generates, so as to operate in conjunction with the movement of the walker's leg, thus assisting a walker in making a walking movement. At this time, it is necessary to adjust the level or timing of the motive power in accordance with walker's walking characteristics (hereinafter also referred to as "gait").

Patent Literature (PTL) 1 discloses a movement assistance system, etc., which calculates time-series data of user's amount of exercise by using a sensor terminal fitted onto the user and predicts a user's daily amount of exercise.

CITATION LIST

Patent Literature

[PTL 1] Japanese Unexamined Patent Application Publication No. 2012-090651

SUMMARY OF INVENTION

Technical Problem

There is, however, the problem that there has been no appropriate algorithm for the walking assistance devices to determine the level, timing, etc., of motive power to be generated in conjunction with a walker's movement (hereinafter also referred to as a walk algorithm) to provide walking assistance.

The movement assistance system disclosed in PTL 1 presents a predicted user's amount of exercise to a user, but does not determine the level or timing of user's movements. Thus, PTL 1 does not solve the aforementioned problem.

The present invention is conceived in order to solve the aforementioned existing problem and has an object to provide a gait data management system, etc., which in order to generate a walk algorithm, appropriately manages gait data to be used when the walking assistance device provides walking assistance.

Solution to Problem

In order to solve the aforementioned problem, a gait data management system according to an aspect of the present invention includes: a server; and a plurality of walking assistance devices, each of which assists a walker in walking, wherein the server includes: an obtaining unit configured to obtain, from each of the plurality of walking assistance devices, a first sensor value obtained when the walker walks with assistance from the walking assistance device; and an accumulating unit configured to accumulate the first sensor value obtained by the obtaining unit, and each of the plurality of walking assistance devices includes: a joint; an actuator that drives the joint; a storage unit in which a walk algorithm is stored, the walk algorithm being an algorithm for determining a drive level of the actuator and being generated through statistical processing on gait data indicating walking characteristics and calculated from the first sensor value accumulated in the accumulating unit; a sensor that obtains a second sensor value obtained when the walker walks with assistance from the walking assistance device; a control unit configured to determine the drive level of the actuator according to the second sensor value using the walk algorithm; and a transmitting unit configured to transmit the second sensor value to the server.

With this, the gait data management system is capable of accumulating, in a server, sensor values obtained when each of the plurality of walking assistance devices provides walking assistance, and assisting a walker in walking by using the walking assistance device according to the walk algorithm generated on the basis of the accumulated sensor values. Since the walk algorithm is generated on the basis of the sensor values obtained when the plurality of walking assistance devices actually provided walking assistance, the possible feeling of discomfort which a walker may have upon receiving walking assistance can be further reduced. Thus, the gait data management system is capable of appropriately managing gait data to be used when a walking assistance device provides walking assistance, in order to generate a walk algorithm.

Examples of a device using a technique similar to the walking assistance device include an autonomous walking device which autonomously walks. A walk algorithm for the autonomous walking device is for determining a motion of a joint, etc., of the autonomous walking device, but the autonomous walking device walks independently of a human walking movement. In contrast, in the walking assistance device, it is necessary to provide walking assistance in conjunction with a human (that is, walker's) walking movement. Thus, the walk algorithm for the walking assistance device is different from that for the autonomous walking device in that the motion of a joint, etc., of the walking assistance device needs to be determined so as to be in conjunction with a walker's walking movement. In addition, since the walking assistance device is fitted onto a walker, the walking assistance device is different from the autonomous walking device in that the possible feeling of discomfort for a walker needs to be as little as possible.

For example, the obtaining unit is configured to obtain, as the first sensor value, the second sensor value transmitted by the transmitting unit, and when a new walk algorithm is generated through statistical processing on a gait value calculated from the second sensor value obtained, the new walk algorithm generated is stored into the storage unit.

Thus, the server efficiently obtains the sensor value from the walking assistance device via communication. Subsequently, the walking assistance device provides walking assistance according to the walk algorithm generated on the basis of the sensor values obtained from the plurality of walking assistance devices including the walking assistance device itself. In this way, a series of events in the flow for generating a new walk algorithm from a newly obtained sensor value takes place in the gait data management system. Thus, the gait data management system is capable of appropriately managing gait data to be used when a walking assistance device provides walking assistance, in order to generate a walk algorithm.

For example, a standard walk algorithm which is a predetermined normal walk algorithm is further stored in the storage unit, and the control unit is further configured to determine the drive level of the actuator according to the second sensor value using the standard walk algorithm when the walk algorithm is not used.

Accordingly, the walking assistance device is capable of providing walking assistance using a predetermined standard walk algorithm. In the case where, for example, the number of sensor values obtained from the walking assistance device is not sufficient, it may be difficult to generate an appropriate walk algorithm on the basis of such sensor values. In such a case, the walking assistance device is capable of providing walking assistance using the predetermined standard walk algorithm.

For example, the transmitting unit is configured to transmit the second sensor value to the server together with model information indicating a model of the walking assistance device, the obtaining unit is configured to obtain the first sensor value together with the model information from each of the plurality of walking assistance devices, the accumulating unit is configured to accumulate the first sensor value in association with the model information obtained by the obtaining unit, and among one or more walk algorithms, each of which is the walk algorithm and generated for one kind of model information, a walk algorithm that fits the model of the walking assistance device is stored in the storage unit.

Thus, the walk algorithm is generated for each model of the walking assistance device. As a result, a walk algorithm suitable for walking assistance is generated for each model of the walking assistance device. This allows the walking assistance device to further reduce the possible feeling of discomfort which a walker may have upon receiving walking assistance.

For example, the sensor includes at least one of an acceleration sensor that obtains an acceleration of the walking assistance device, an angle sensor that obtains an angle of rotation of the joint, and a pressure sensor that obtains a pressure applied from a back of a foot of the walker.

With this, the walking assistance device determines a drive level of an actuator on the basis of the acceleration of the walking assistance device, the angle of rotation of a joint of the walking assistance device, and the pressure applied from the back of a walker's foot. Furthermore, a walk algorithm for determining a more accurate drive level of the actuator can be generated on the basis of these acceleration, angle of rotation, and pressure. This allows the walking assistance device to further reduce the possible feeling of discomfort which a walker may have upon receiving walking assistance.

For example, the walk algorithm generated through the statistical processing that is a process of calculating a mean, a median, or a mode of the first sensor value accumulated in the accumulating unit is stored in the storage unit.

Thus, the walking assistance device is capable of providing walking assistance using the walk algorithm generated specifically through the process of calculating the mean, the median, or the mode.

For example, the walk algorithm that includes at least one of walk algorithms for assisting the walker in level walking, uphill walking, and downhill walking is stored in the storage unit, the sensor further includes an air pressure sensor, and the control unit is further configured to (i) determine, on the basis of a change in an altitude of the walking assistance device at a current position determined from a sensor value of the air pressure sensor, whether the walker walks on a level ground, uphill, or downhill, (ii) select an appropriate walk algorithm from among a plurality of the walk algorithms stored in the storage unit, and (iii) determine the drive level of the actuator according to the walk algorithm selected.

Thus, the walking assistance device is capable of providing walking assistance using the walk algorithm generated for each type of walk (specifically, level walking, uphill walking, and downhill walking). This allows the walking assistance device to further reduce the possible feeling of discomfort which a walker may have upon receiving walking assistance.

Furthermore, a walking assistance device according to an aspect of the present invention is a walking assistance device included in a plurality of walking assistance devices, each of which assists a walker in walking, in a gait data management system including: a server; and the plurality of walking assistance devices, the server including: an obtaining unit configured to obtain, from each of the plurality of walking assistance devices, a first sensor value obtained when the walker walks with assistance from the walking assistance device; and an accumulating unit configured to accumulate the first sensor value obtained by the obtaining unit, the walking assistance device including: a joint; an actuator that drives the joint; a storage unit in which a walk algorithm is stored, the walk algorithm being an algorithm for determining a drive level of the actuator and being generated through statistical processing on gait data indicating walking characteristics and calculated from the first sensor value accumulated in the accumulating unit; a sensor that obtains a second sensor value obtained when the walker walks with assistance from the walking assistance device; a control unit configured to determine the drive level of the actuator according to the second sensor value using the walk algorithm; and a transmitting unit configured to transmit the second sensor value to the server.

With this, the same advantageous effects as the gait data management system described above are produced.

Furthermore, a server according to an aspect of the present invention is a server included in a gait data management system including: the server; and a plurality of walking assistance devices, each of which assists a walker in walking, the server including: an obtaining unit configured to obtain, from each of the plurality of walking assistance devices, a first sensor value obtained when the walker walks with assistance from the walking assistance device; and an accumulating unit configured to accumulate the first sensor value obtained by the obtaining unit, wherein each of the plurality of walking assistance devices includes: a joint; an actuator that drives the joint; a storage unit in which a walk algorithm is stored, the walk algorithm being an algorithm for determining a drive level of the actuator and being generated through statistical processing on gait data indicating walking characteristics and calculated from the first sensor value accumulated in the accumulating unit; a sensor that obtains a second sensor value obtained when the walker walks with assistance from the walking assistance device; a control unit configured to determine the drive level of the actuator according to the second sensor value using the walk algorithm; and a transmitting unit configured to transmit the second sensor value to the server.

With this, the same advantageous effects as the gait data management system described above are produced.

Furthermore, a gait data management method according to an aspect of the present invention is a gait data management method for a gait data management system including: a server; and a plurality of walking assistance devices, each of which assists a walker in walking, the gait data management method including: obtaining, from each of the plurality of walking assistance devices, a first sensor value obtained when the walker walks with assistance from the walking assistance device; and accumulating the first sensor value obtained in the obtaining, wherein each of the plurality of walking assistance devices includes: a joint; an actuator that drives the joint; a storage unit in which a walk algorithm is stored, the walk algorithm being an algorithm for determining a drive level of the actuator; and a sensor that obtains a second sensor value obtained when the walker walks with assistance from the walking assistance device, and the gait data management method further includes: calculating gait data from the first sensor value accumulated in the accumulating, the gait data indicating walking characteristics; generating a walk algorithm through statistical processing on the gait data calculated in the calculating; determining the drive level of the actuator according to the second sensor value using the walk algorithm; and transmitting the second sensor value to the server.

With this, the same advantageous effects as the gait data management system described above are produced.

These general and specific aspects may be implemented using a system, a method, an integrated circuit, a computer program, or a computer-readable recording medium such as a compact disc read-only memory (CD-ROM), or any combination of systems, methods, integrated circuits, computer programs, or recording media.

Advantageous Effects of Invention

The gait data management system according to the present invention is capable of appropriately managing gait data to be used when a walking assistance device provides walking assistance, in order to generate a walk algorithm.

BRIEF DESCRIPTION OF DRAWINGS

FIG. 10 illustrates gait values for different types of walk according to Variation 1 of Embodiment 1.

FIG. 11 illustrates gait values for different body types according to Variation 2 of Embodiment 1.

DESCRIPTION OF EMBODIMENTS

Note that each of the following embodiments describes a specific preferred example of the present invention. The numerical values, shapes, materials, structural elements, the arrangement and connection of the structural elements, steps, the processing order of the steps etc. shown in the following embodiments are mere examples, and are not intended to limit the scope of the present invention. Furthermore, among the structural elements in the following embodiments, structural elements not recited in the independent claims indicating the broadest concept of the present invention are described as arbitrary structural elements of a more preferable embodiment.

Note that the same structural elements are assigned the same reference signs, and overlapping description may be omitted.

Embodiment 1

In the present embodiment, a description will be given of a gait data management system, etc., which in order to generate a walk algorithm, appropriately manages gait data to be used when the walking assistance device provides walking assistance.

Figure 1:
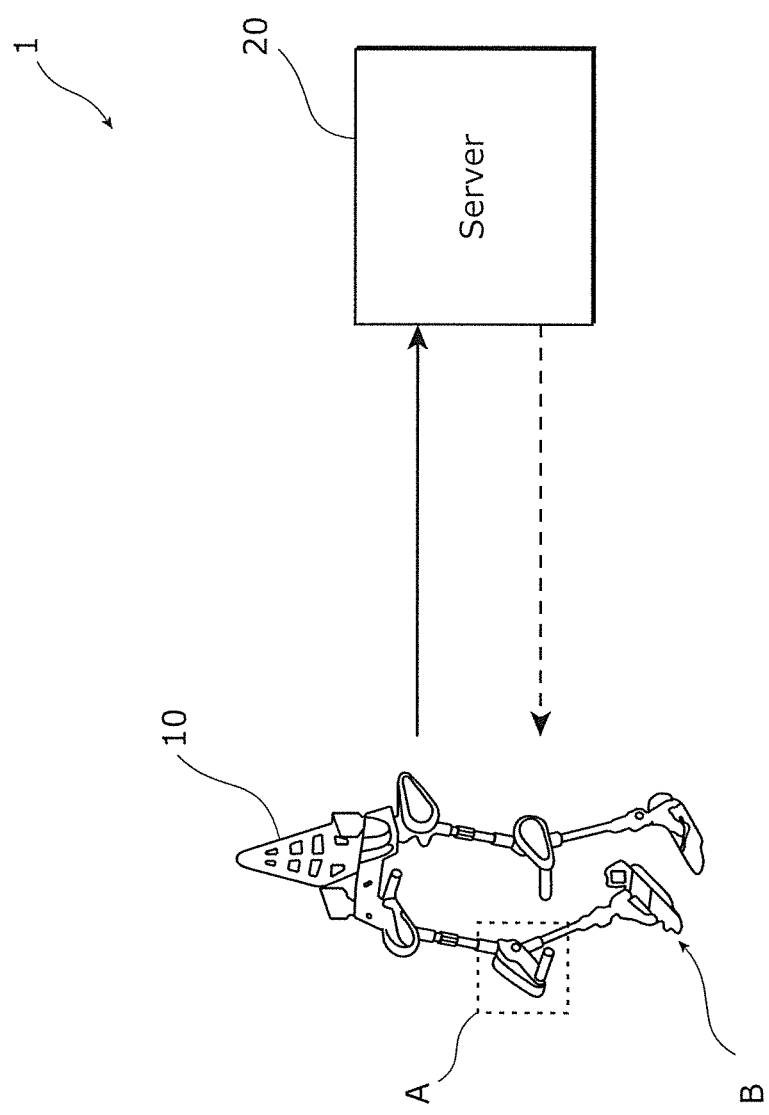
FIG. 1 is a schematic system diagram of a gait data management system according to Embodiment 1.

FIG. 1 is a system configuration diagram of a gait data management system 1 according to the present embodiment.

As illustrated in FIG. 1, the gait data management system 1 includes a walking assistance device 10 and a server 20. The walking assistance device 10 and the server 20 are connected by a communication line.

The walking assistance device 10 assists a walker in making a walking movement (hereinafter also referred to simply as "walking"). The walking assistance device 10 includes: frames formed from a rigid member; a joint that rotatably connects the frames to each other; and an actuator serving as a driving device for rotating the frames connected to the joint.

The walking assistance device 10 is fitted onto a walker and assists the walker in walking by operating according to an algorithm for providing walking assistance (hereinafter also referred to as a walk algorithm) in conjunction with a walker's movement.

Specifically, the walking assistance device 10 causes the actuator to generate rotational force at the joint, thereby controlling the angle of the joint and driving the frames to assist a walker in walking.

The walking assistance device 10 includes a plurality of sensors that detects the angle of the joint and the like. Each of the plurality of sensors obtains a sensor value when walking assistance is provided, and transmits the obtained sensor value to the server 20 through the communication line. Furthermore, the walking assistance device 10 updates the walk algorithm by an appropriate method.

The server 20 obtains the sensor values from the walking assistance device 10 and accumulates the sensor values. The server 20 obtains the sensor values from more than one walking assistance device 10. Note that the server 20 may manages the sensor values in association with the product types, etc., of the walking assistance devices 10.

Furthermore, the server 20 provides the accumulated sensor values in response to an obtainment request. The obtainment request is issued by, for example, a developer or a maintenance personnel for the walking assistance device 10.

Figure 2:
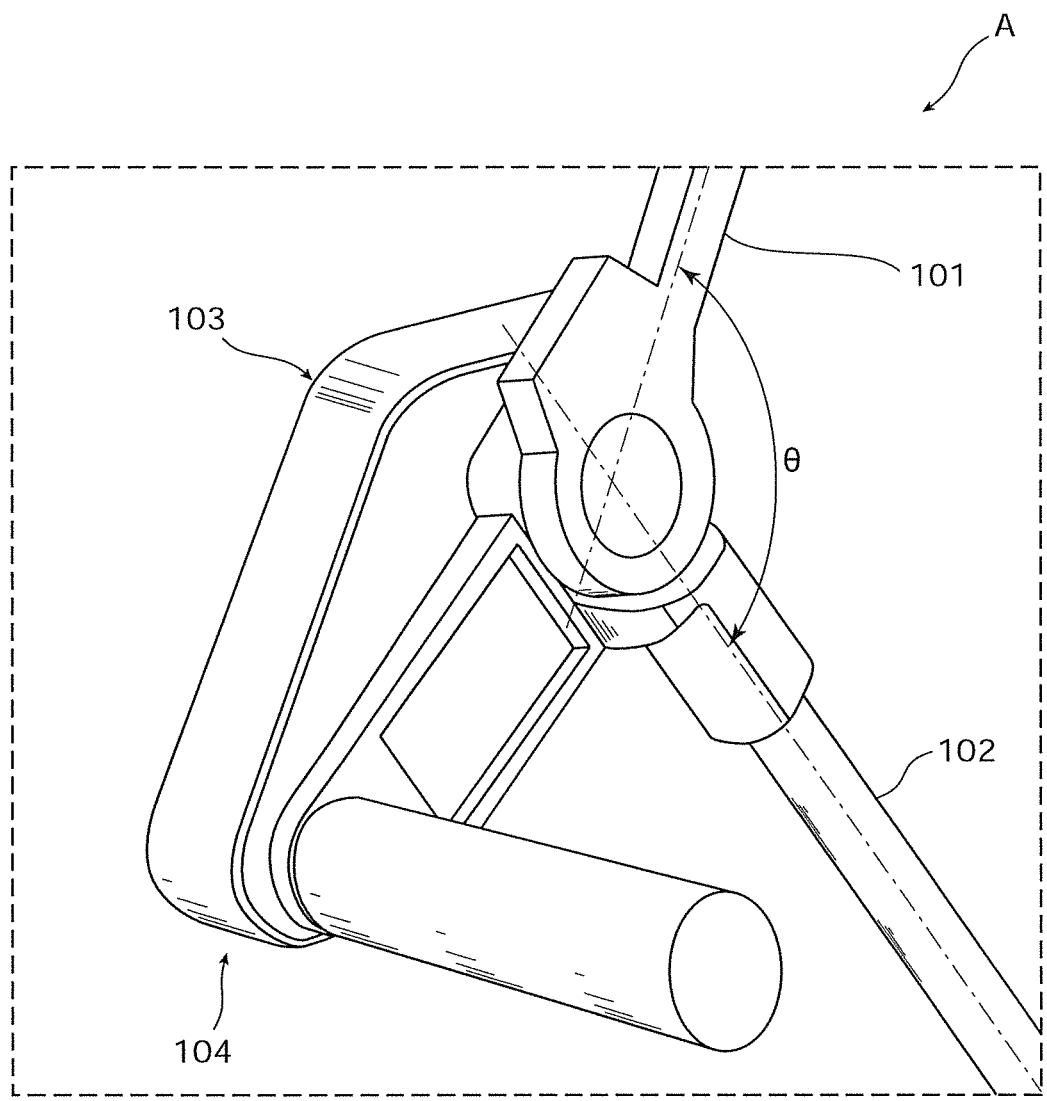
FIG. 2 illustrates a joint of a walking assistance device according to Embodiment 1.

FIG. 2 illustrates the joint of the walking assistance device 10 according to the present embodiment. The joint of the walking assistance device 10 will be described with reference to FIG. 2. FIG. 2 is an enlarged view of the inside of the portion in the dashed line box denoted as A in FIG. 1.

As illustrated in FIG. 2, the walking assistance device 10 includes frames 101 and 102, a joint 103, and an actuator 104.

The frames 101 and 102 are rigid components. The frames 101 and 102 are two frames connected via the joint 103 among frames included in the walking assistance device 10. Although two frames 101 and 102 are illustrated as an example, other frames are also connected via a joint as just described.

The joint 103 is a rotating mechanism that is rotatably connected to the frames 101 and 102. The joint 103 is provided in a position, for example, near the left-side waist, the right-side waist, the left knee, the right knee, the left lateral malleolus (ankle), or the right lateral malleolus (ankle) of a walker fitted with the walking assistance device 10. Hereinafter, the angle at the joint 103 between the frame 101 and the frame 102 will be referred to as an angle of rotation θ.

The actuator 104 is a driving device that generates motive power necessary for walking assistance. The actuator 104 includes a motor and a power source for driving the motor.

The actuator 104 is a driving device that drives the frames 101 and 102 relatively by changing the degree of the angle of rotation θ of the joint 103 by an appropriate degree at an appropriate timing. The walking assistance device 10 assists a walker in walking as a result of the actuator 104 and other actuators included in the walking assistance device 10 driving the frames in conjunction with each other.

Figure 3:
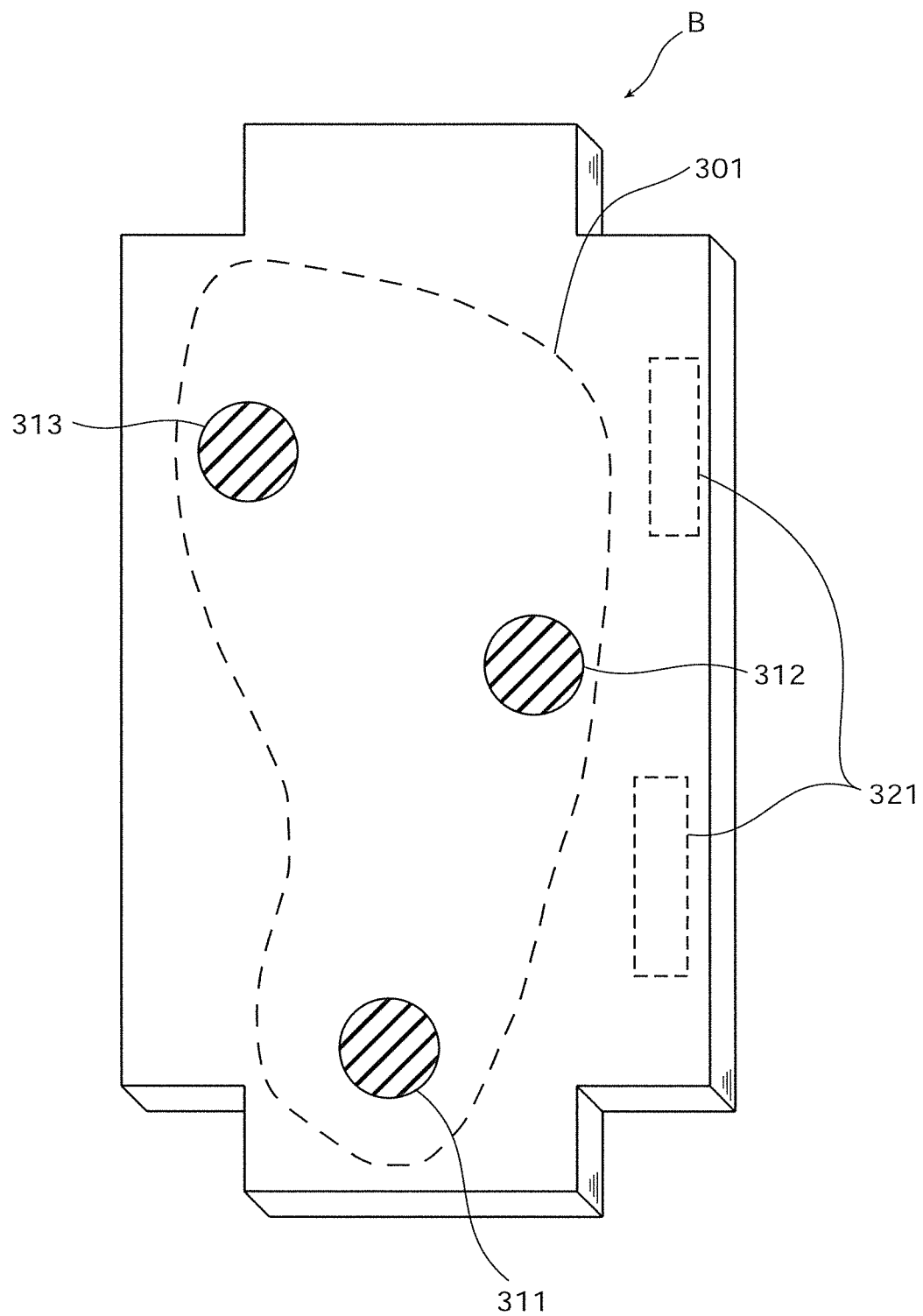
FIG. 3 illustrates a pressure sensor of a walking assistance device according to Embodiment 1.

FIG. 3 illustrates a pressure sensor of the walking assistance device 10 according to the present embodiment. FIG. 3 illustrates a sole plate which is denoted as B in FIG. 1 and on which the back of a walker's foot is placed.

As illustrated in FIG. 3, the sole plate includes three pressure sensors 311, 312, and 313. In FIG. 3, an outline 301 is the outline of an area in which the back of a walker's foot is expected to be placed. An outline 321 indicates a position in which the frame is connected to the sole plate.

The pressure sensor 311 is provided in a position in which a walker's heel is expected to be placed. The pressure sensor 313 is provided in a position in which a walker's toe is expected to be placed. The pressure sensor 312 is provided in a position in which a part of the area between walker's heel and toe that is other than the arch of walker's foot, which is less likely to bear walker's body weight, is expected to be placed.

The walking assistance device 10 is capable of detecting a walking movement or a walking state of a walker on the basis of pressure values detected by the above three pressure sensors 311, 312, and 313. Specifically, for example, when the pressure values detected by each of the three pressure sensors 311, 312, and 313 are temporarily substantially constant, the detection result shows that the walker is standing and not in motion. When the pressure value of the pressure sensor 313 increases while each of the three pressure sensors 311, 312, and 313 detects temporarily substantially constant pressure values, the detection results shows that the standing walker not in motion is about to start walking forward. When the pressure value of the pressure sensor 311 increases while each of the three pressure sensors 311, 312, and 313 detects temporarily substantially constant pressure values, the detection results shows that the standing walker not in motion is about to start walking backward.

Figure 4:
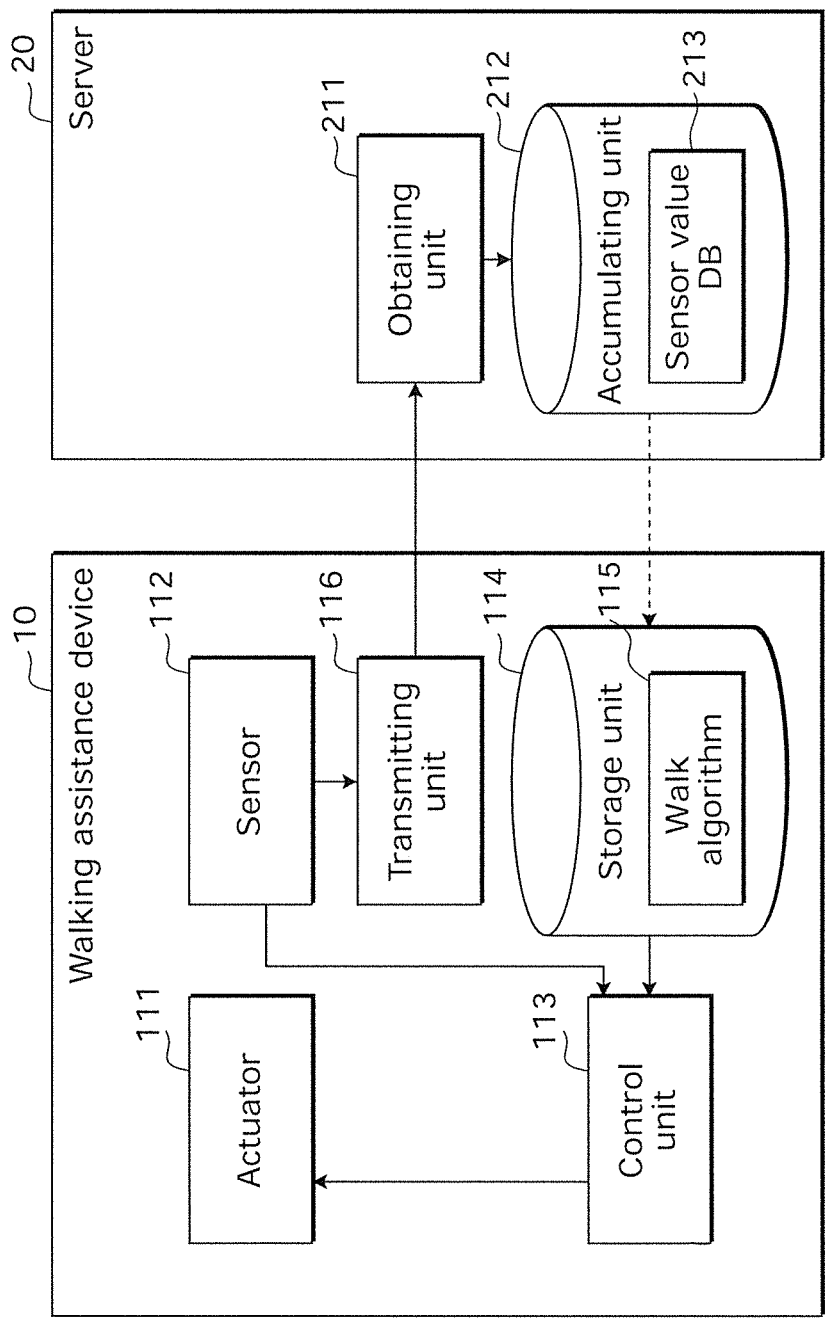
FIG. 4 is a function block diagram of a gait data management system according to Embodiment 1.

FIG. 4 is a function block diagram of the gait data management system 1 according to the present embodiment.

As illustrated in FIG. 4, the gait data management system 1 includes the walking assistance device 10 and the server 20.

The walking assistance device 10 includes an actuator 111, a sensor 112, a control unit 113, a storage unit 114, and a transmitting unit 116.

The storage unit 114 stores a walk algorithm 115 generated through statistical processing on a gait value that indicates a gait of the walker and is calculated from the sensor value (a first sensor value) accumulated in an accumulating unit 212 (a sensor value DB 213) of the server 20. The gait value is also referred to as gait data.

Furthermore, when a sensor value is newly obtained, a new walk algorithm 115 generated through statistical processing on a gait value calculated from the newly obtained sensor value is stored into the storage unit 114. As a result, the storage unit 114 is holding the new walk algorithm.

Furthermore, a standard walk algorithm which is a predetermined normal walk algorithm may be stored in the storage unit 114. The standard walk algorithm is, for example, a walk algorithm for assisting a person of a normal body type in making a walking movement.

The gait value indicates walker's walking characteristics; examples of the gait value include a stride and a walking period. Furthermore, a value of a stride or the like of each of left and right legs may be used as the gait value, and a value of a single stride or the like without distinction between left and right legs may be used as the gait value. The walk algorithm 115 is an algorithm for determining a drive level and a drive timing of the actuator 111 from the sensor value obtained from the sensor 112. In other words, the walk algorithm 115 includes information indicating which joint is to be driven at which timing to what extent in order to assist a walker in walking.

The walk algorithm 115 stored in the storage unit 114 is an algorithm generated on the basis of the sensor value accumulated in the accumulating unit 212 of the server 20. Specifically, the walk algorithm 115 is an algorithm derived by calculating information including walker's walking stride and period from the sensor value accumulated in the accumulating unit 212 of the server 20, and performing statistical processing on the calculated information. The statistical processing includes the process of calculating the mean, the median, or the mode, for example. The statistical processing may be performed on the basis of input from a user or may be automatically performed by an information processing device or the like according to a predetermined procedure.

It is also possible to generate the walk algorithm 115 through the process of generating, out of the calculated information, information including one set of the stride and the period by a predetermined method, instead of the statistical processing. Note that a value indicating walker's walking characteristics, such as the stride or the period, is also referred to as a gait value.

The actuator 111 is a driving device that generates motive power necessary for walking assistance and corresponds to the actuator 104 in FIG. 2. Specifically, the actuator 111 is a driving device that generates motive power for rotating the frames connected to the joint of the walking assistance device 10. The control unit 113 determines a drive level of the actuator 111. The actuator 111 is exemplified as a motor that is driven with power.

The sensor 112 obtains a sensor value when a walker walks with assistance of the motive power generated by the actuator 111. Specifically, the sensor 112 includes at least one of an acceleration sensor that obtains an acceleration of the walking assistance device 10, an angle sensor that obtains an angle of rotation of the joint of the walking assistance device 10, and a pressure sensor that obtains a pressure in a predetermined position on the back of a walker's foot. The acceleration sensor can be provided in any position on the walking assistance device 10. The acceleration sensor is provided, for example, in a position in which the acceleration sensor is less susceptible to the effect of forward and backward leg movement when walking assistance is provided and in which the acceleration sensor contacts the walker's back waist when fitted onto the walker. Note that the sensor value obtained by the sensor 112 when the walker walks with assistance of the motive power generated by the actuator 111 is also referred to as a second sensor value.

The control unit 113 is a control circuit that determines, using the walk algorithm 115, a drive level of the actuator 111 according to the sensor value obtained by the sensor 112. Specifically, when the control unit 113 determines on the basis of the sensor value obtained by the sensor 112 that the walker is walking, the control unit 113 determines a drive level and a drive timing for the actuator 111 to drive the joint according to the walk algorithm 115. The control unit 113 then drives the actuator 111 by the determined drive level at the determined timing.

When the walk algorithm 115 is not used, the control unit 113 may use the standard walk algorithm stored in the storage unit 114 to determine a drive level of the actuator 111 according to the sensor value. There can be various cases as the case in which the walk algorithm 115 is not used; examples thereof include a case in which non-use of the walk algorithm 115 in the walking assistance for a walker is set by the walker.

The transmitting unit 116 transmits, to the server 20, the sensor value obtained by the sensor 112. Specifically, the transmitting unit 116 transmits, to the server 20, the sensor value obtained by the sensor 112 when the walking assistance device 10 assists a walker in walking by the control unit 113 driving the actuator 111 according to the walk algorithm 115. The transmitting unit 116 transmits information to the server 20 using a communication interface suitable for the communication line connecting the walking assistance device 10 and the server 20. The communication line may have any specification; for example, a wireless local area network (LAN), a mobile phone network, a public communication network, or the like may be used.

The server 20 includes an obtaining unit 211 and an accumulating unit 212.

The obtaining unit 211 obtains, from the plurality of walking assistance devices 10, the sensor values obtained when a walker walks with assistance from each walking assistance device 10. Specifically, the obtaining unit 211 obtains the sensor values transmitted by the transmitting unit 116 of the walking assistance device 10 through the communication line. The sensor value obtained by the server 20 from the walking assistance device 10 is also referred to as a first sensor value.

The accumulating unit 212 is a storage device in which the sensor value obtained by the obtaining unit 211 is accumulated. Specifically, the accumulating unit 212 accumulates, in the sensor value DB 213, the sensor value obtained by the obtaining unit 211, as data. Note that when the data accumulated in the sensor value DB 213 reaches a predetermined data amount or more, the accumulating unit 212 may delete part of the accumulated data or may transfer part of the accumulated data to another storage device. The data to be deleted or transferred may be data obtained at an earlier point in time than a predetermined point in time or may be data obtained by a predetermined model of the walking assistance device.

The relationship between the first sensor value and the second sensor value is supplementally described below. As described above, the first sensor value is a sensor value obtained by the server 20 from the walking assistance device 10, and the second sensor value is a sensor value obtained by the sensor 112. In the gait data management system 1, the sensor value and the walk algorithm are exchanged between the walking assistance device 10 and the server 20. This exchange can be described as below focusing on the sensor value.

The walking assistance device 10 obtains the second sensor value when walking assistance for a walker is provided using the walk algorithm 115, and transmits the obtained second sensor value to the server 20. The server 20 receives, as the first sensor value, the second sensor value transmitted by the walking assistance device 10, and accumulates the received first sensor value. Thereafter, the walking assistance device 10 obtains the walk algorithm 115 newly generated on the basis of the first sensor value accumulated in the server 20, and assists the walker in walking by using the obtained new walk algorithm 115.

By performing this flow repeatedly, the gait data management system 1 is capable of updating the walk algorithm 115 on the basis of the sensor value obtained when walking assistance for a walker is provided.

Note that in the case where there are more than one model of the walking assistance devices 10, the walk algorithm may be generated for each of the models. Specifically, the transmitting unit 116 transmits the sensor value to the server 20 together with model information indicating the model of the walking assistance device 10. The obtaining unit 211 obtains the sensor value from each of the plurality of walking assistance devices 10 together with the model information. The accumulating unit 212 accumulates the sensor value in accordance with the model information obtained by the obtaining unit 211. Among one or more walk algorithms, each of which is generated for one kind of model information, the walk algorithm that fits the model of the walking assistance device 10 is stored in the storage unit 114. In this way, the gait data management system 1 is capable of generating, for each model, the walk algorithm that reflects a difference in model, and assisting a walker in walking by using the generated walk algorithm.

Figure 5:
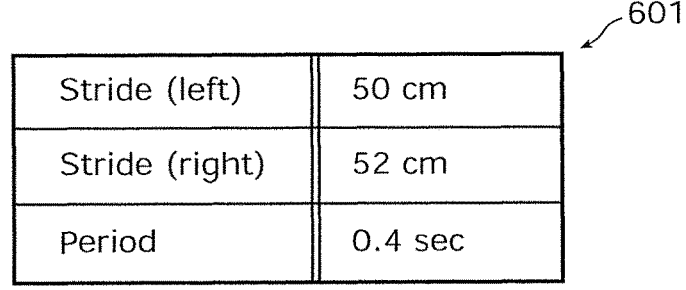
FIG. 5 illustrates sensor values according to Embodiment 1.

FIG. 5 illustrates sensor values according to the present embodiment. A sensor value column 501 illustrated in FIG. 5 indicates an example of more than one sensor value obtained by the sensor 112 of the walking assistance device 10.

The sensor value column 501 indicates an angle of rotation θ obtained at predetermined time intervals by the angle sensor of the walking assistance device 10 which is provided on the walker's side waist. It is sufficient that the predetermined time interval be so short that a variation in the angle of rotation θ due to walking of the walker is measured; for example, the predetermined time interval can be 0.1 seconds.

For example, in the case where the walker swings his or her leg forward for walking and then, the leg swung forward approaches the walker's body as the walker's body moves forward by walking, the value becomes "30°" when the leg is swung forward, and then the value changes as follows: "29°, 27°, . . . ", as the leg swung forward approaches the walker's body. In such a case, the sensor value column 501 illustrated in FIG. 5 is obtained.

In the case where the angle sensor is located on each of walker's left-side waist and right-side waist, sensor value columns including respective sensor values obtained from the left and right angle sensors are obtained. In the case where the angle sensor is provided in positions other than the walker's side waist as well, the sensor value column is obtained for each sensor.

Figure 6:
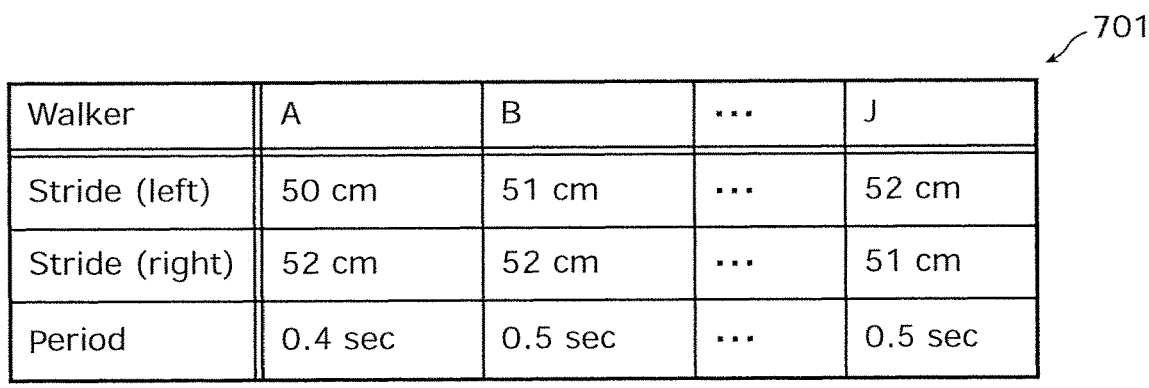
FIG. 6 illustrates gait values according to Embodiment 1.

FIG. 6 illustrates the gait value according to the present embodiment. A gait value 601 illustrated in FIG. 6 is one example of the gait value which indicates the gait of the walker walking with the walking assistance device 10 fitted thereto and is calculated from the sensor value column 501 illustrated in FIG. 5.

The gait value 601 includes the stride of the left leg ("Stride (left)"), the stride of the right leg ("Stride (right)"), and the period.

The stride is a quantity indicating the distance from a first landing point to a second landing point when one of the walker's feet lands on the first landing point and then the other foot lands on the second landing point. There is generally a difference in the stride even between single person's left and right legs. It is possible to obtain a more accurate gait of a walker by calculating each of the stride of the left leg and the stride of the right leg.

The difference between the stride of the left leg and the stride of the right leg, however, can be considered to be so small that one of the strides or the mean of the strides may be regarded as the stride of the walker. In this way, the amount of communication from the walking assistance device 10 to the server 20 and the data storage capacity of the server 20 can be reduced.

The stride may be a quantity indicating the distance from a first landing point to a second landing point when one of the walker's feet lands on the first landing point and then separates from the ground and subsequently, the walker's foot lands on the second landing point.

The period is a quantity indicating time from when one of the walker's feet landed on the ground separates from the ground for walking to when the walker's foot lands on the ground again. Alternatively, the period may be a quantity indicating time from when one of the walker's feet lands on the ground to when the other walker's foot lands on the ground. Similarly to the stride, there is generally a difference in the period even between single person's left and right legs, and the difference can be considered to be negligible.

Note that a single gait value 601 is calculated from a single sensor value column 501. In this regard, a plurality of sensor value columns included in a single sensor value column 501 (hereinafter also referred to as "partial sensor value columns") can be regarded as the sensor value column 501. In this case, a single gait value 601 is calculated from a single partial sensor value column. Thus, there are instances where more than one gait value 601 is calculated from a single sensor value column 501.

Figure 7:
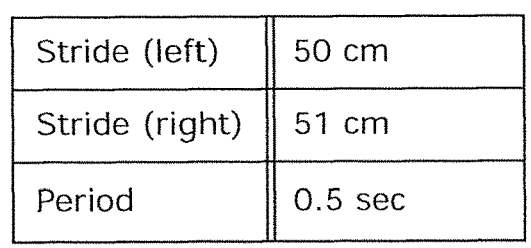
FIG. 7 illustrates statistical processing on gait values according to Embodiment 1.

FIG. 7 illustrates statistical processing on the gait values according to the present embodiment.

FIG. 7 illustrates a plurality of gait values 701 and a gait value 702 which is a result of statistical processing.

The plurality of gait values 701 include a gait value obtained when each of walkers (A, B, . . . , J) walks with assistance from the walking assistance device 10. This shows that there are small differences in the values of the stride and the period between the walkers.

The gait value 702 is derived through the statistical processing on gait values included in the plurality of gait values 701. The statistical processing is performed, for example, through the process of taking the mean of the gait values of each type. Note that the statistical processing may be performed through the process of taking the median or the mode, instead of taking the mean, of the gait values of each type.

Figure 8:
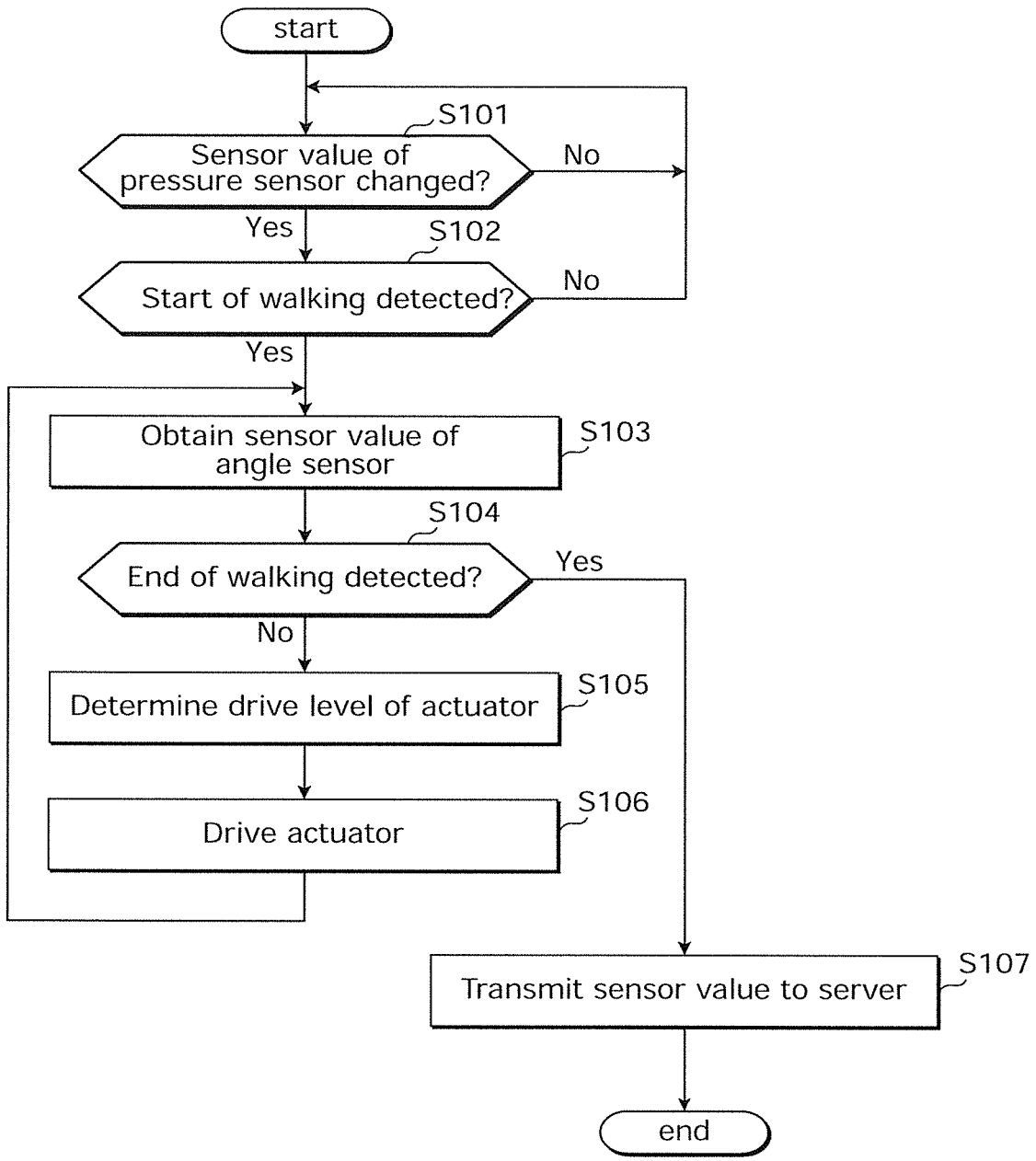
FIG. 8 is a flowchart illustrating the processing performed by a walking assistance device according to Embodiment 1.

FIG. 8 is a flowchart illustrating the processing performed by the walking assistance device 10 according to the present embodiment. The flowchart illustrated in FIG. 8 indicates a series of events in the flow from when the walking assistance device 10 is fitted onto a walker and then the walker who is not in walking motion starts walking until when the walker later stops walking. The process in Step S101 is performed while the walker is not in walking motion.

In Step S101, the control unit 113 determines whether or not the sensor value of the pressure sensor which is the sensor 112 has been changed. Specifically, the pressure sensor repeatedly detects a sensor value while the walker fitted with the walking assistance device 10 is not in walking motion. When the difference between the current and last sensor values detected by the pressure sensor is greater than or equal to a predetermined value, the control unit 113 detects a change in the sensor value of the pressure sensor.

When the control unit 113 determines in Step S101 that the sensor value of the pressure sensor has been changed, the processing proceeds to Step S102. When the control unit 113 determines that the sensor value of the pressure sensor has not been changed, Step S101 is repeated. This means that the control unit 113 repeats Step S101 until it determines that the sensor value of the pressure sensor has been changed. In other words, the control unit 113 remains in a standby state until it determines that the sensor value of the pressure sensor has been changed.

In Step S102, on the basis of the sensor value of the pressure sensor obtained in Step S101, the control unit 113 determines whether or not the walker fitted with the walking assistance device 10 has started walking. A start of the walking is determined, for example, on the basis of a change in the sensor values of more than one pressure sensor.

For example, in the case where the sensor 112 includes the three pressure sensors 311, 312, and 313 illustrated in FIG. 3, when the sensor value of the pressure sensor 311 (the pressure sensor provided in a position in which a walker's heel is expected to be placed) is lower than the last measurement value and the sensor value of the pressure sensor 313 (the pressure sensor provided in a position in which a walker's toe is expected to be placed) is higher than the last measurement value, the control unit 113 determines that the walker has started walking forward. When the sensor value of the pressure sensor 311 is higher than the last measurement value and the sensor value of the pressure sensor 313 is lower than the last measurement value in the situation just described, the control unit 113 can determine that the walker has started walking backward.

When the control unit 113 detects a start of walking in Step S102, the processing proceeds to Step S103. When the control unit 113 does not detect a start of walking, Step S101 is repeated.

In Step S103, the control unit 113 obtains the sensor value of the angle sensor which is the sensor 112. The sensor value of the angle sensor indicates an angle formed between frames connected to a joint of the walking assistance device 10 (for example, the angle of rotation θ formed between the frames 102 and 103 connected to the joint 103). The control unit 113 obtains the sensor value of the angle sensor to recognize what attitude the walking assistance device 10 is assuming and what posture the walker fitted with the walking assistance device 10 is assuming.

In Step S104, the control unit 113 determines whether or not the walker fitted with the walking assistance device 10 has finished walking. An end of the walking is determined, for example, on the basis of a change in the sensor values of more than one pressure sensor.

For example, in the case where the sensor 112 includes the three pressure sensors 311, 312, and 313 illustrated in FIG. 3, when the sensor value of each of the three pressure sensors is not zero and is approximately the same as the last measurement value, the control unit 113 determines that the walker has finished walking.

When the control unit 113 detects an end of walking in Step S104, the processing proceeds to Step S107. When the control unit 113 does not detect an end of walking, that is, when the control unit 113 detects that the walking continues, the processing proceeds to Step S105.

In Step S105, the control unit 113 determines, using the walk algorithm 115, a drive level of the actuator 111 according to the sensor value obtained in Step S103. The sensor value obtained in Step S103 is information that can be used to determine the positional relationship between the frames of the walking assistance device 10. According to the walk algorithm, the positional relationship of the frames of the walking assistance device 10 at the next point in time is determined on the basis of the current positional relationship of the frames determined from the sensor value described above. In this way, the control unit 113 determines the attitude of the walking assistance device 10 to be assumed at the next point in time from the current attitude thereof.

In Step S106, the actuator 111 is driven to cause the walking assistance device 10 to assist the walker in walking. The drive level of the actuator 111 is determined in Step S105 and is appropriate for changing the attitude of the walking assistance device 10 into the attitude to be assumed at the next point in time.

When the process in Step S106 ends, the walking assistance device 10 repeats Step S104.

In Step S107, the transmitting unit 116 transmits, to the server 20, the sensor value obtained by the sensor 112 when the walking assistance device 10 provides walking assistance. The sensor value to be transmitted is the sensor value repeatedly obtained in Step S103 during the period of time in which the walking assistance continues. For example, the sensor value to be transmitted includes more than one value of angle obtained by the angle sensor.

Note that Step S107 may be performed once every time a series of the processes from Step S101 to Step S106 is completed as illustrated in FIG. 5 or may be performed once every time a series of the processes from Step S101 to Step S106 is completed more than one time.

As described above, a series of events in the flow from when a walker starts walking until the end of the walking takes place.

Figure 9:
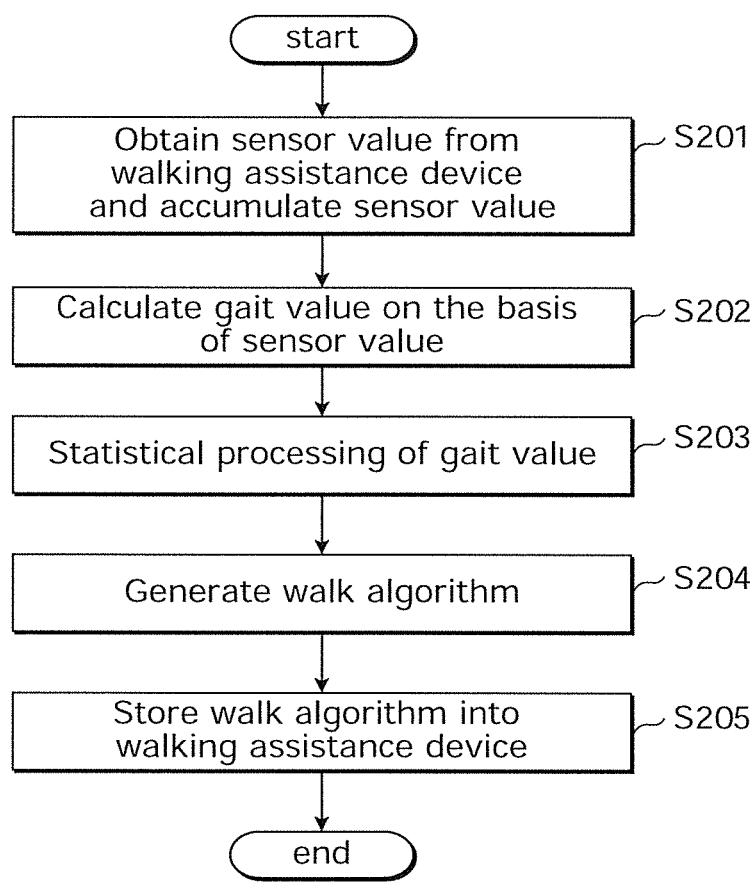
FIG. 9 is a flowchart illustrating the processing performed by a server, etc., according to Embodiment 1.

FIG. 9 is a flowchart illustrating the processing of updating the walk algorithm performed by the server 20, etc., according to the present embodiment. The processing performed by the server 20, etc., will be described with reference to FIG. 9.

In Step S201, the obtaining unit 211 obtains a sensor value from the walking assistance device 10 and accumulates the obtained sensor value in the accumulating unit 212. The sensor value that is obtained by obtaining unit 211 includes more than one sensor value obtained by the angle sensor and is, for example, the sensor value column 501 illustrated in FIG. 5. Every time the obtaining unit 211 obtains a sensor value from the walking assistance device 10, the obtaining unit 211 accumulates the obtained sensor value in the accumulating unit 212. As a result, sensor values obtained by the walking assistance device 10 in different periods of time are accumulated in the accumulating unit 212, and sensor values obtained from two or more walking assistance devices 10 can be accumulated.

In Step S202, a gait value is calculated on the basis of the sensor value obtained in Step S201. Note that the process of calculating a gait value may be performed by the server 20 or the like using a predetermined calculation method or may be performed manually. The calculated gait value is, for example, the gait value 601 illustrated in FIG. 6.

In Step S203, the statistical processing on the gait value calculated in Step S202 is performed. The gait value to be subject to the statistical processing is the gait value calculated in Step S202 for each of the sensor value columns obtained from the plurality of walking assistance devices 10 and then accumulated; the number of gait values to be subject to the statistical processing is equal to the number of sensor value columns. In the statistical processing described above, a single gait value is calculated from as many gait values as the sensor value columns. Note that the process of calculating a single gait value may be performed by the server 20 or the like using a predetermined calculation method or may be performed manually.

In Step S204, a walk algorithm is generated on the basis of the single gait value calculated in Step S203. Stated differently, the single gait value calculated in Step S203 indicates a single normal gait determined on the basis of the gait of a walker who walked using the walking assistance device 10 from which the sensor value column was obtained. In Step S204, a walk algorithm for providing walking assistance for a walker walking with the single normal gait is generated. Note that the process of generating a walk algorithm may be performed by the server 20 or the like using a predetermined method or may be performed manually using an arbitrary information processing device.

In Step S205, the walk algorithm generated in Step S204 is stored into the walking assistance device 10. Specifically, the walk algorithm generated in Step S204 is stored into the storage unit 114 of the walking assistance device 10 as the walk algorithm 115. Note that in the case where there is any previously stored walk algorithm 115 in the storage unit 114, the walk algorithm generated in Step S204 is stored so as to be preferentially referred to.

The process of storing a walk algorithm may be performed through a communication line or the like between the server 20, etc., and the walking assistance device 10. In the case where the walk algorithm is manually generated using the information processing device in Step S204, the walk algorithm in the information processing device may be manually stored into the walking assistance device 10 using a portable recording medium or the like.

As described above, a series of processes for updating the walk algorithm in the server 20, etc., is performed.

As described above, the gait data management system 1 according to the present embodiment includes: the server 20; and the plurality of walking assistance devices 10, each of which assists a walker in walking, the server 20 includes: the obtaining unit 211 that obtains, from each of the plurality of walking assistance devices 10, the first sensor value obtained when the walker walks with assistance from the walking assistance device 10; and the accumulating unit 212 that accumulates the first sensor value obtained by the obtaining unit 211, and each of the plurality of walking assistance devices 10 includes: the joint; the actuator 111 that drives the joint; the storage unit 114 that stores the walk algorithm 115 that is an algorithm for determining a drive level of the actuator 111 and is generated through the statistical processing on the gait data indicating the walking characteristics and calculated from the first sensor value accumulated in the accumulating unit 212; the sensor that obtains the second sensor value obtained when the walker walks with assistance from the walking assistance device 10; the control unit 113 that determines a drive level of the actuator 111 according to the second sensor value using the walk algorithm 115; and the transmitting unit 116 that transmits the second sensor value to the server 20.

With this, the gait data management system 1 is capable of accumulating, in the server 20, the sensor values obtained when each of the plurality of walking assistance devices 10 provides walking assistance, and assisting a walker in walking by using the walking assistance device 10 according to the walk algorithm 115 generated on the basis of the accumulated sensor values. Since the walk algorithm 115 is generated on the basis of the sensor values obtained when the plurality of walking assistance devices 10 actually provided walking assistance, the possible feeling of discomfort which a walker may have upon receiving walking assistance can be further reduced. Thus, the gait data management system 1 is capable of appropriately managing gait data to be used when the walking assistance device 10 provides walking assistance, in order to generate the walk algorithm 115.

Examples of a device using a technique similar to the walking assistance device 10 include an autonomous walking device which autonomously walks. A walk algorithm for the autonomous walking device is for determining a motion of a joint, etc., of the autonomous walking device, but the autonomous walking device walks independently of a human walking movement. In contrast, in the walking assistance device 10, it is necessary to provide walking assistance in conjunction with a human (that is, walker's) walking movement. Thus, the walk algorithm 115 for the walking assistance device 10 is different from that for the autonomous walking device in that the motion of a joint, etc., of the walking assistance device 10 needs to be determined so as to be in conjunction with a walker's walking movement. In addition, since the walking assistance device is fitted onto a walker, the walking assistance device is different from the autonomous walking device in that the possible feeling of discomfort for a walker needs to be as little as possible.

For example, the obtaining unit 211 obtains, as the first sensor value, the second sensor value transmitted by the transmitting unit 116, and when a new walk algorithm 115 is generated through the statistical processing on the gait value calculated from the obtained second sensor value, the generated new walk algorithm 115 is stored into the storage unit 114.

Thus, the server 20 efficiently obtains the sensor values from the walking assistance device 10 via communication. Subsequently, the walking assistance device 10 provides walking assistance according to the walk algorithm generated on the basis of the sensor values obtained from the plurality of walking assistance devices 10 including the walking assistance device 10 itself. In this way, a series of events in the flow for generating a new walk algorithm 115 from a newly obtained sensor value takes place in the gait data management system 1. Thus, the gait data management system 1 is capable of appropriately managing gait data to be used when the walking assistance device 10 provides walking assistance, in order to generate a walk algorithm.

For example, a standard walk algorithm which is a predetermined normal walk algorithm 115 is further stored in the storage unit 114, and the control unit 113 further determines the drive level of the actuator 111 according to the second sensor value using the standard walk algorithm when the walk algorithm 115 is not used.

Accordingly, the walking assistance device 10 is capable of providing walking assistance using a predetermined standard walk algorithm. In the case where, for example, the number of sensor values obtained from the walking assistance device 10 is not sufficient, it may be difficult to generate an appropriate walk algorithm 115 on the basis of such sensor values. In such a case, the walking assistance device 10 is capable of providing walking assistance using the predetermined standard walk algorithm.

For example, the transmitting unit 116 transmits the second sensor value to the server 20 together with model information indicating the model of the walking assistance device 10, the obtaining unit 211 obtains the first sensor value together with the model information from each of the plurality of walking assistance devices 10, the accumulating unit 212 accumulates the first sensor value in association with the model information obtained by the obtaining unit 211, and among one or more walk algorithms 115, each of which is generated for one kind of model information, a walk algorithm that fits the model of the walking assistance device 10 is stored in the storage unit 114.

Thus, the walk algorithm 115 is generated for each model of the walking assistance device 10. As a result, a walk algorithm suitable for walking assistance is generated for each model of the walking assistance device 10. This allows the walking assistance device 10 to further reduce the possible feeling of discomfort which a walker may have upon receiving walking assistance.

For example, the sensor 112 includes at least one of an acceleration sensor that obtains an acceleration of the walking assistance device 10, an angle sensor that obtains an angle of rotation of the joint, and a pressure sensor that obtains a pressure applied from the back of a walker's foot.

With this, the walking assistance device 10 determines a drive level of the actuator 111 on the basis of the acceleration of the walking assistance device 10, the angle of rotation of a joint of the walking assistance device 10, and the pressure applied from the back of a walker's foot. Furthermore, the walk algorithm 115 for determining a more accurate drive level of the actuator 111 can be generated on the basis of these acceleration, angle of rotation, and pressure. This allows the walking assistance device 10 to further reduce the possible feeling of discomfort which a walker may have upon receiving walking assistance.

For example, the walk algorithm 115 generated through the statistical processing that is the process of calculating the mean, the median, or the mode of the first sensor value accumulated in the accumulating unit 212 is stored in the storage unit 114.

Thus, the walking assistance device 10 is capable of providing walking assistance using the walk algorithm 115 generated specifically through the process of calculating the mean, the median, or the mode.

Variation 1 of Embodiment 1

Embodiment 1 has described the case where in the gait data management system, the sensor values obtained from the plurality of walking assistance devices 10 are used to calculate a single gait value and generate a single walk algorithm. The present variation will describe the case where in the gait data management system, a plurality of gait values corresponding to different types are calculated, and walk algorithms respectively corresponding to the plurality of calculated gait values are generated.

FIG. 10 illustrates gait values of different types of walk according to the present variation.

As illustrated in FIG. 10, a walk type table 1001 according to the present variation includes more than one type including, for example, a "Level walking" type 1011, an "Uphill walking" type 1012, and a "Downhill walking" type 1013. Hereinafter, the "Level walking" type will be also referred to simply as "level walking". The same applies to the "Uphill walking" and the "Downhill walking".

The level walking 1011 is a gait value indicating the gait of a walker when the walker walks on the level ground. The gait in the level walking 1011 is the gait of a walker when the walking assistance device 10 assists the walker in walking on the level ground.

The uphill walking 1012 is a gait value indicating the gait of a walker when the walker walks up an ascending slope. The gait in the uphill walking 1012 is the gait of a walker when the walking assistance device 10 assists the walker in walking up an ascending slope. Note that in the gait value in the uphill walking 1012, for example, the stride tends to be smaller than that in the level walking 1011, but the technical scope of the present invention is not limited to this example.

The downhill walking 1013 is a gait value indicating the gait of a walker when the walker walks down a descending slope. The gait in the downhill walking 1013 is the gait of a walker when the walking assistance device 10 assists the walker in walking down a descending slope. Note that in the gait value in the "uphill walking", for example, the stride tends to be small and the period tends to be relatively short compared with those in the "level walking", but the technical scope of the present invention is not limited to this example.

Examples of the type of gait other than those stated above include "load-carrying level walking", "load-carrying uphill walking", and "load-carrying downhill walking". These types of gait mean that a walker walks in the form of "level walking", "uphill walking", and "downhill walking", respectively, while carrying a load (a heavy object).

In this way, the walk algorithm for use in the walk assistance which the walking assistance device 10 provides is generated on the basis of the gait value indicating the gait of each type of walk (Step S204 in FIG. 9).

In the present variation, the walking assistance device 10 includes an air pressure sensor as the sensor 112. The air pressure sensor obtains the surrounding air pressure.

The control unit 113 calculates an altitude of the walking assistance device 10 at the current location from the air pressure obtained by the air pressure sensor of the sensor 112. On the basis of variations between the calculated altitudes, the control unit 113 determines whether the walker walks on the level ground, uphill, or downhill, then selects an appropriate walk algorithm from among the walk algorithms stored in the storage unit 114, and determines a drive level of the actuator 111 according to the selected walk algorithm. This allows the walking assistance device 10 to provide walking assistance according to the type of walk of a walker.

As described above, in the walking assistance system according to the present variation, the walk algorithm 115 that includes at least one of the walk algorithms for assisting the walker in level walking, uphill walking, and downhill walking is stored in the storage unit 114, the sensor 112 further includes an air pressure sensor, and the control unit 113 (i) determines, on the basis of a change in an altitude of the walking assistance device 10 at a current position determined from the sensor value of the air pressure sensor, whether the walker walks on the level ground, uphill, or downhill, (ii) selects an appropriate walk algorithm 115 from among the plurality of walk algorithms 115 stored in the storage unit 114, and (iii) determines a drive level of the actuator 111 according to the selected walk algorithm 115.

Thus, the walking assistance system is capable of providing walking assistance using the walk algorithm 115 generated for each type of walk (specifically, level walking, uphill walking, and downhill walking). This allows the walking assistance device 10 to further reduce the possible feeling of discomfort which a walker may have upon receiving walking assistance.

Variation 2 of Embodiment 1

The present variation will describe the case where in the gait data management system, a plurality of gait values corresponding to the body type of a walker are calculated, and walk algorithms respectively corresponding to the plurality of calculated gait values are generated.

FIG. 11 illustrates a gait value table 1101 indicating gait values for different body types according to the present variation. In FIG. 11, an example in which the body height is used as an index indicating a body type is illustrated.

As illustrated in FIG. 11, there are a plurality of body types according to the present variation, including a "Short height" type 1111, a "Medium height" type 1112, and a "High height" type 1113, for example. Hereinafter, the "Short height" type will be also referred to simply as "short height". The same applies to the "Medium height" and the "High height".

The short height 1111 and the high height 1113 indicate that a walker is shorter and higher in height, respectively, than a predetermined height, and the medium height 1112 indicates that a walker has a height between the short height 1111 and the high height 1113. Note that the height at the border between the medium height 1112 and the short height 1111 or the high height 1113 is arbitrarily determined and can be any numerical value that indicates a body height at which the entire walkers can be significantly classified into more than one group. For example, a walker who is shorter than 150 cm may be classified as the short height 1111, a walker who is not shorter than 150 cm and shorter than 160 cm may be classified as the medium height 1112, and a walker who is not shorter than 160 cm may be classified as the high height 1113.

Note that although the number of body types is set to three in the above example, the number of body types may be other than three. When the number of body types is set to more than three, it is possible to provide walking assistance using a walk algorithm that matches the body type of the walker more accurately.

Although only the body height is used as the body type in the example illustrated above, this is not the only example. Specifically, the leg length can also be used. Furthermore, it is also possible to generate a walk algorithm for each walker. This allows the walking assistance device to generate a walk algorithm for providing walking assistance in conjunction with the gait of a walker with increased accuracy and thus provide more accurate walking assistance in conjunction with the gait of the walker.

In this way, the walk algorithm for use in the walk assistance which the walking assistance device 10 provides is generated on the basis of the gait value indicating the gait of a walker of each body type (Step S204 in FIG. 9). This allows the walking assistance device 10 to provide walking assistance according to the body type of a walker.

As described above, the walking assistance device according to the present variation is capable of providing walking assistance using a walk algorithm that matches a walker more accurately.

Embodiment 2

The present embodiment will describe examples of the walking assistance device 10 and an improved device thereof and information such as a gait value and a walk algorithm that are exchanged between a user and a plurality of business entities, etc.

Figure 12:
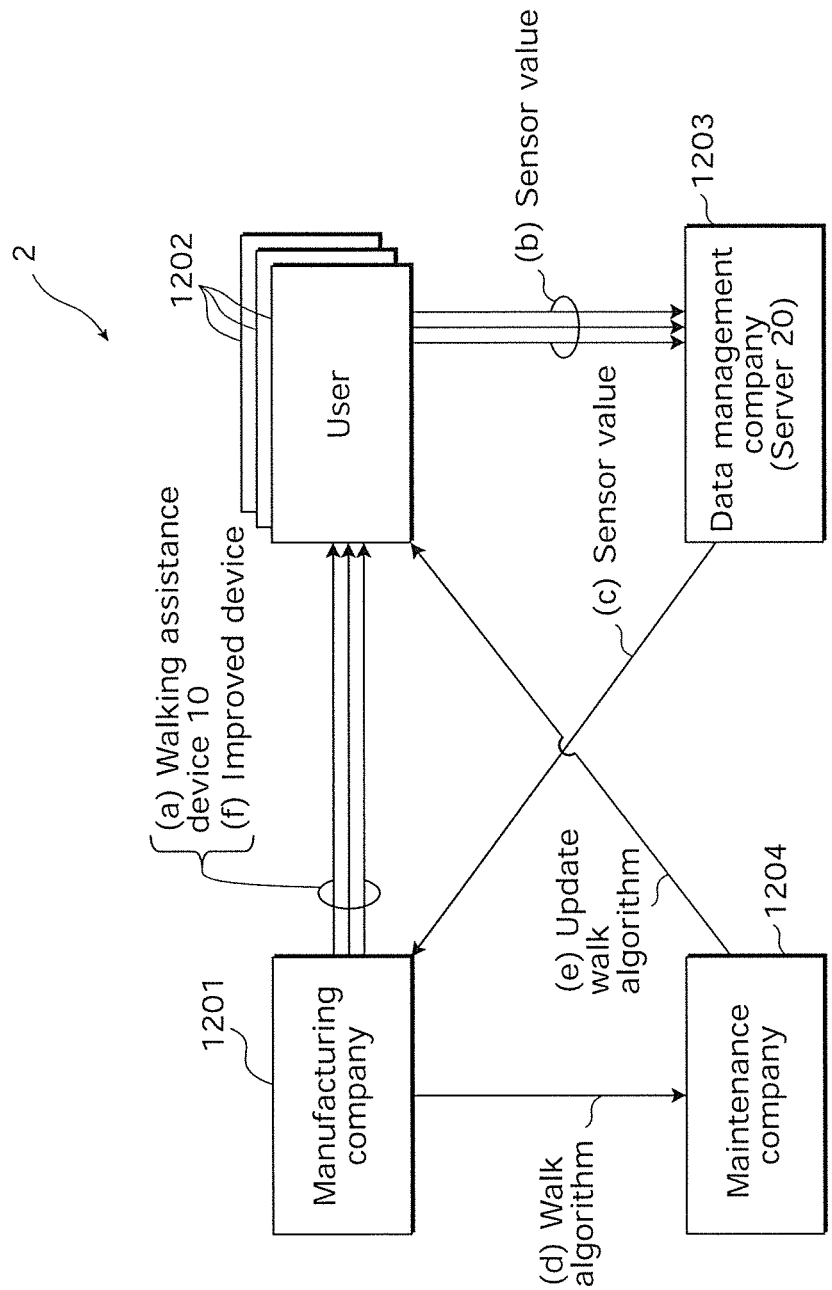
FIG. 12 schematically illustrates devices and the flow of information in a gait data management system according to Embodiment 2.

FIG. 12 is a system configuration diagram of a gait data management system 2 according to the present embodiment.

As illustrated in FIG. 12, the gait data management system 2 includes a manufacturing company 1201, a data management company 1203, and a maintenance company 1204. In FIG. 12, a user 1202 who uses the above gait data management system 2 is also illustrated.

The manufacturing company 1201 is a business entity that manufactures and improves the walking assistance device 10. The manufacturing company 1201 provides the manufactured walking assistance device 10 or improved device (hereinafter also referred to simply as "the device") to the user 1202.

The user 1202 is provided with the device from the manufacturing company 1201 and walks as a walker with assistance from the walking assistance device 10.

The data management company 1203 is a business entity that manages the server 20 that accumulates the sensor value. The data management company 1203 possesses the server 20.

The maintenance company 1204 is a business entity that provides maintenance for the walking assistance device 10.

The following describes a series of events in the flow from when the walking assistance device 10 is provided until when the walk algorithm is updated or when an improved device is provided.

In (a) of FIG. 12, the manufacturing company 1201 provides the walking assistance device 10 to the user 1202.

In (b) of FIG. 12, the sensor value of the walking assistance device 10 obtained when the user 1202 walked is transmitted from the walking assistance device 10 to the server 20 through a communication line. The sensor value to be transmitted is the sensor value of the walking assistance device 10 obtained when the user provided with the walking assistance device 10 from the manufacturing company 1201 walked as a walker with assistance from the walking assistance device 10.

In (c) of FIG. 12, the sensor value is provided from the server 20 to the manufacturing company 1201. There are various methods of providing the sensor value. In one example of the methods, the manufacturing company 1201 transmits, to the data management company 1203, a request for obtaining the sensor value, and the data management company 1203 provides the sensor value accumulated in the server 20. Note that the transmission of the request, the obtainment of the sensor value, etc., just described may be achieved through a communication line or may be achieved manually.

In (d) of FIG. 12, the manufacturing company 1201 provides the walk algorithm to the maintenance company. The walk algorithm to be provided to the maintenance company is a walk algorithm resulting from statistical processing, etc., on the sensor value obtained by the manufacturing company 1201 from the data management company 1203 (Step S204 in FIG. 9).

In (e) of FIG. 12, the walk algorithm is updated. Specifically, the maintenance company 1204 is provided with the walk algorithm for the walking assistance device 10 from the manufacturing company 1201 and stores the provided walk algorithm into the walking assistance device 10 possessed by each user 1202. Thus, the walking assistance device 10 operates so as to assist the walker in walking using the stored walk algorithm.

In (f) of FIG. 12, the manufacturing company 1201 provides the improved device of the walking assistance device 10 to the user 1202. The improved device means the next version of the walking assistance device 10 and includes a device produced by adding a new function to the existing or past walking assistance device 10, a device produced by solving the trouble or problem of the existing or past walking assistance device 10, and a device produced by improving the design of the existing or past walking assistance device 10. A sales company may mediate when the manufacturing company 1201 provides the device to the user 1202.

Either (e) or (f) of FIG. 12 may come first, or it may be possible that only one of (e) and (f) of FIG. 12 is performed.

As described above, according to the gait data management system according to the present embodiment, the walking assistance device 10 and the improved device thereof and the information such as the gait value and the walk algorithm are appropriately exchanged between the user and the plurality of business entities.

Although the walking assistance device, etc., in the present invention is described thus far based on the embodiments, the present invention is not limited to the embodiments. Various modifications of the present embodiments as well as embodiments resulting from combinations of structural elements of the different embodiments that may be conceived by those skilled in the art may be included within the scope of the present invention as long as these do not depart from the essence of the present invention.

INDUSTRIAL APPLICABILITY

The present invention is available to a gait data management system which in order to generate a walk algorithm, appropriately manages gait data to be used when a walking assistance device provides walking assistance.

REFERENCE SIGNS LIST 1, 2 gait data management system
10 walking assistance device
20 server
101, 102 frame
103 joint
104, 111 actuator
112 sensor
113 control unit
114 storage unit
115 walk algorithm
116 transmitting unit
211 obtaining unit
212 accumulating unit 213 sensor value DB
311, 312, 313 pressure sensor
1201 manufacturing company
1202 user
1203 data management company
1204 maintenance company

The invention claimed is:

1. A gait data management system comprising:
a server; and
a plurality of walking assistance devices, each of which assists a walker in walking, wherein the server includes:
an obtaining unit configured to obtain, from each of the plurality of walking assistance devices, a first sensor value obtained when the walker walks with assistance from the walking assistance device; and
an accumulating unit configured to accumulate the first sensor value obtained by the obtaining unit, and
each of the plurality of walking assistance devices includes:
a joint;
an actuator that drives the joint;
a storage unit in which a walk algorithm is stored, the walk algorithm being an algorithm for determining a drive level of the actuator and being generated through statistical processing on gait data indicating walking characteristics and calculated from the first sensor value accumulated in the accumulating unit;
a sensor that obtains a second sensor value obtained when the walker walks with assistance from the walking assistance device;
a control unit configured to determine the drive level of the actuator according to the second sensor value using the walk algorithm; and
a transmitting unit configured to transmit the second sensor value to the server.

2. The gait data management system according to claim 1, wherein the obtaining unit is configured to obtain, as the first sensor value, the second sensor value transmitted by the transmitting unit, and
when a new walk algorithm is generated through statistical processing on a gait value calculated from the second sensor value obtained, the new walk algorithm generated is stored into the storage unit.

3. The gait data management system according to claim 1, wherein a standard walk algorithm which is a predetermined normal walk algorithm is further stored in the storage unit, and
the control unit is further configured to determine the drive level of the actuator according to the second sensor value using the standard walk algorithm when the walk algorithm is not used.

4. The gait data management system according to claim 2, wherein the transmitting unit is configured to transmit the second sensor value to the server together with model information indicating a model of the walking assistance device,
the obtaining unit is configured to obtain the first sensor value together with the model information from each of the plurality of walking assistance devices,
the accumulating unit is configured to accumulate the first sensor value in association with the model information obtained by the obtaining unit, and
among one or more walk algorithms, each of which is the walk algorithm and generated for one kind of model information, a walk algorithm that fits the model of the walking assistance device is stored in the storage unit.

5. The gait data management system according to claim 1, wherein the sensor includes at least one of an acceleration sensor that obtains an acceleration of the walking assistance device, an angle sensor that obtains an angle of rotation of the joint, and a pressure sensor that obtains a pressure applied from a back of a foot of the walker.

6. The gait data management system according to claim 1, wherein the walk algorithm generated through the statistical processing that is a process of calculating a mean, a median, or a mode of the first sensor value accumulated in the accumulating unit is stored in the storage unit.

7. The gait data management system according to claim 1, wherein the walk algorithm that includes at least one of walk algorithms for assisting the walker in level walking, uphill walking, and downhill walking is stored in the storage unit,
the sensor further includes an air pressure sensor, and
the control unit is further configured to (i) determine, on the basis of a change in an altitude of the walking assistance device at a current position determined from a sensor value of the air pressure sensor, whether the walker walks on a level ground, uphill, or downhill, (ii) select an appropriate walk algorithm from among a plurality of the walk algorithms stored in the storage unit, and (iii) determine the drive level of the actuator according to the walk algorithm selected.

8. A walking assistance device included in a plurality of walking assistance devices, each of which assists a walker in walking, in a gait data management system including: a server; and the plurality of walking assistance devices, the server including: an obtaining unit configured to obtain, from each of the plurality of walking assistance devices, a first sensor value obtained when the walker walks with assistance from the walking assistance device; and an accumulating unit configured to accumulate the first sensor value obtained by the obtaining unit, the walking assistance device comprising:
a joint;
an actuator that drives the joint;
a storage unit in which a walk algorithm is stored, the walk algorithm being an algorithm for determining a drive level of the actuator and being generated through statistical processing on gait data indicating walking characteristics and calculated from the first sensor value accumulated in the accumulating unit;
a sensor that obtains a second sensor value obtained when the walker walks with assistance from the walking assistance device;
a control unit configured to determine the drive level of the actuator according to the second sensor value using the walk algorithm; and
a transmitting unit configured to transmit the second sensor value to the server.

9. A server included in a gait data management system including: the server; and a plurality of walking assistance devices, each of which assists a walker in walking, the server comprising:
an obtaining unit configured to obtain, from each of the plurality of walking assistance devices, a first sensor value obtained when the walker walks with assistance from the walking assistance device; and
an accumulating unit configured to accumulate the first sensor value obtained by the obtaining unit,
wherein each of the plurality of walking assistance devices includes:

a joint;
an actuator that drives the joint;
a storage unit in which a walk algorithm is stored, the walk algorithm being an algorithm for determining a drive level of the actuator and being generated through statistical processing on gait data indicating walking characteristics and calculated from the first sensor value accumulated in the accumulating unit;
a sensor that obtains a second sensor value obtained when the walker walks with assistance from the walking assistance device;
a control unit configured to determine the drive level of the actuator according to the second sensor value using the walk algorithm; and
a transmitting unit configured to transmit the second sensor value to the server.

* * * * *

UNITED STATES PATENT AND TRADEMARK OFFICE
CERTIFICATE OF CORRECTION

PATENT NO. : 10,543,143 B2
APPLICATION NO. : 15/509743
DATED : January 28, 2020
INVENTOR(S) : Asano et al.

It is certified that error appears in the above-identified patent and that said Letters Patent is hereby corrected as shown below:

In the Specification

In Column 20, Lines 53-67, should be deleted; and

In Column 21, Lines 1-6, should be deleted.

Signed and Sealed this
Twelfth Day of May, 2020

Andrei Iancu
*Director of the United States Patent and Trademark Office*